US011109986B2

(12) United States Patent
Smith et al.

(10) Patent No.: US 11,109,986 B2
(45) Date of Patent: *Sep. 7, 2021

(54) TORQUE MEASURING SPRING FOR A PROSTHETIC DRIVE

(71) Applicant: Ottobock Health Care LP, Austin, TX (US)

(72) Inventors: Weston Smith, Bedford, MA (US); Christopher Morse, Bedford, MA (US); Paul Balutis, Bedford, MA (US)

(73) Assignee: Otto Bock Healthcare LP, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/458,597

(22) Filed: Jul. 1, 2019

(65) Prior Publication Data
US 2019/0321200 A1 Oct. 24, 2019

Related U.S. Application Data

(63) Continuation of application No. 15/694,835, filed on Sep. 3, 2017, now Pat. No. 10,335,292.

(51) Int. Cl.
| *A61F 2/00* | (2006.01) |
| *A61F 2/66* | (2006.01) |
| *A61F 2/68* | (2006.01) |
| *A61F 2/76* | (2006.01) |
| *A61F 2/60* | (2006.01) |
| *A61F 2/50* | (2006.01) |

(52) U.S. Cl.
CPC .......... *A61F 2/66* (2013.01); *A61F 2/68* (2013.01); *A61F 2/76* (2013.01); *A61F 2002/5003* (2013.01); *A61F 2002/5033* (2013.01); *A61F 2002/5072* (2013.01); *A61F 2002/5087* (2013.01); *A61F 2002/607* (2013.01); *A61F 2002/7625* (2013.01); *A61F 2002/7635* (2013.01)

(58) Field of Classification Search
CPC ...... A61F 2/66; A61F 2/68; A61F 2/76; A61F 2002/5003; A61F 2002/5033; A61F 2002/5072; A61F 2002/5087; A61F 2002/607; A61F 2002/7625; A61F 2002/7635
USPC ....................... 73/862.191, 862.181
See application file for complete search history.

(56) References Cited

U.S. PATENT DOCUMENTS

| 5,658,241 A * | 8/1997 | Deharde ............ A61F 5/0123 602/23 |
| 7,857,833 B2 * | 12/2010 | Abdou ............. A61B 17/7071 606/254 |
| 10,335,292 B2 * | 7/2019 | Smith ................ A61F 2/68 |

(Continued)

*Primary Examiner* — Max H Noori
*Assistant Examiner* — Masoud H Noori
(74) *Attorney, Agent, or Firm* — Kacvinsky Daisak Bluni PLLC

(57) ABSTRACT

An improvement to a prosthetic device which provides a spring member between first and second structural members that are rotatably connected to one another, the spring member providing predictable resistance as it is compressed by the rotation of the first and second structural members with respect to each other. The known resistance of the spring is used as an input to a model controlling a motor control circuit to provide counter-torque as rotational torque is applied to compress the spring.

22 Claims, 13 Drawing Sheets

(56) References Cited

U.S. PATENT DOCUMENTS

| | | | |
|---|---|---|---|
| 2004/0153015 A1* | 8/2004 | Seligman | A61F 5/0123 602/16 |
| 2006/0014116 A1* | 1/2006 | Maijer | A61C 7/12 433/11 |
| 2017/0231797 A1* | 8/2017 | LeCursi | A61F 5/0127 602/16 |

* cited by examiner

TORQUE MEASURING SPRING FOR A PROSTHETIC DRIVE

RELATED APPLICATIONS

This application is a continuation application of U.S. Ser. No. 15/694,835, filed on Sep. 3, 2017, entitled "Torque Measuring Spring for a Prosthetic Device', of which is hereby incorporated by reference in its entirety.

TECHNICAL FIELD

Embodiments herein generally relate to the field of prosthetic devices, and, more particularly, to prosthetic devices for lower leg amputees which include an ankle joint.

BACKGROUND

Various known prosthetic devices assist the user in walking by simulating the movement and forces on a human ankle applied by the Achilles tendon and calf muscle as a person walks. In certain cases, a counter-torque is applied to the ankle joint during certain phases of the walking cycle to assist the user. Often the amount of torque is determined by a model or calculation and applied by a motor controlled by the model. To determine the amount of counter-torque that should be applied by the motor, it is necessary to determine the amount of torque that is being applied by the user to flex the ankle joint during normal walking.

DETAILED DESCRIPTION

Figure 1A:
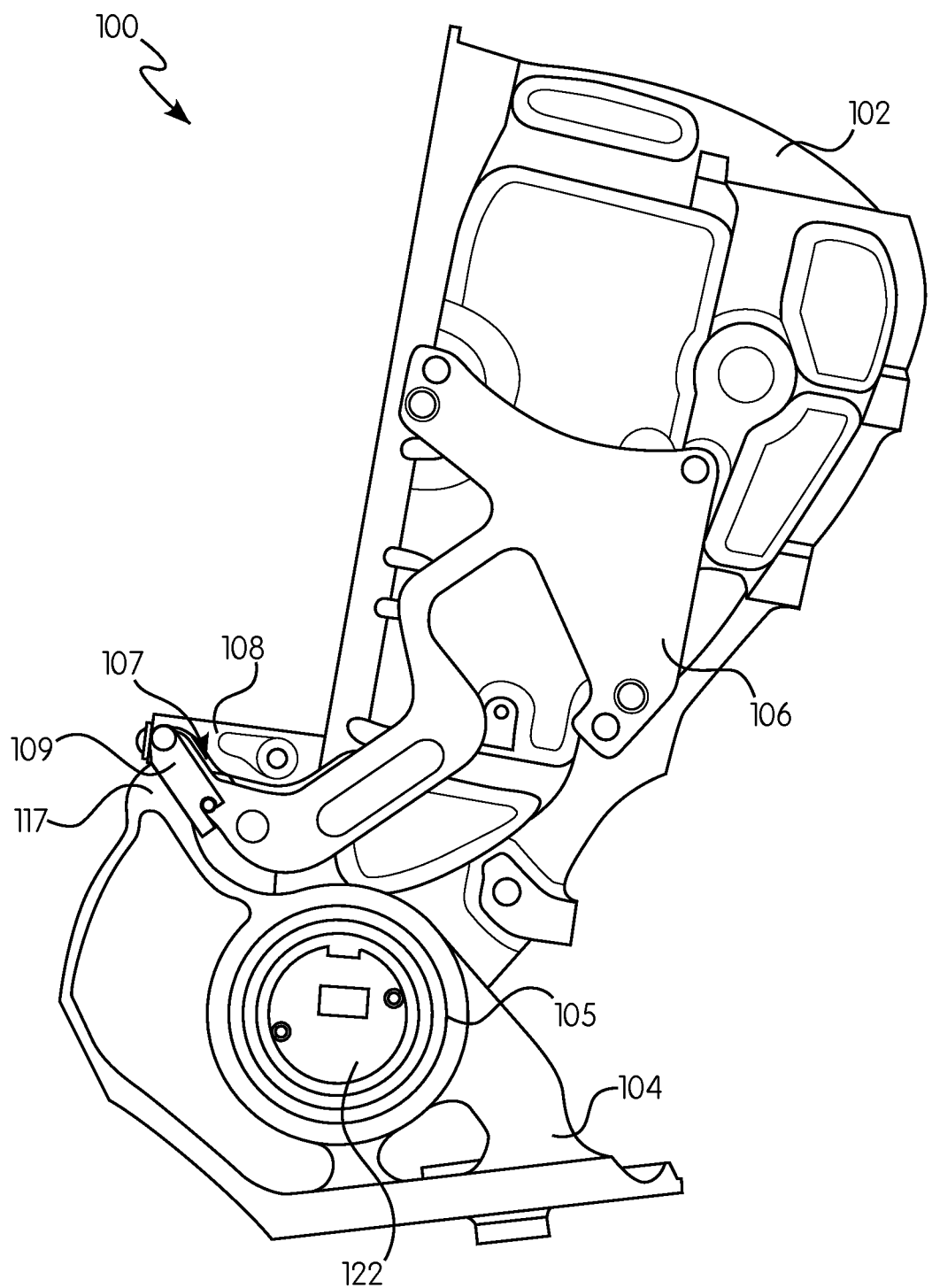
FIG. 1(a) is a side view of a prosthetic device having an embodiment of the force measuring spring of the present invention installed thereon, in a first position.

Modern lower leg prosthetic devices may use an actuator under the control of a control system to provide certain amounts of counter-torque during certain parts of the walking cycle, to make the device better mimic a real human ankle. However, at any given moment, it is necessary to know how much counter-torque the actuator is required to apply.

The force measuring spring of the present invention is used as an input to a model which calculates the amount of counter-torque to be applied to the ankle joint. When the ankle joint rotates to a toe-up position, the rotation causes compression of the force measuring spring. Because the spring constant is known, the rate of deflection of the spring can be used to calculate how much torque is being applied to push the toe up. The rate of the deflection of the spring can be inferred from the rate of rotation of the ankle joint. In some embodiments, the rotation of the ankle joint is measured using a magnetic angle sensor, and thus the rate of rotation can be calculated by the change in angle over time. The calculation of how much torque is being applied is utilized as an input to a model that controls the counter-torque provided by the actuator.

The novel shape of the force measuring spring described herein allows the spring member to deform in a near-linear manner. This helps to reduce the relative motion between the contact surface of the spring and the lower portion of the prosthetic device that contacts the spring to reduce wear on the contact surface, and noise generated by the contact.

In operation, prior to or at the time when the prosthetic device is in a neutral position, the force measuring spring would not be compressed. The neutral position can be defined as the point of relative movement between the upper portion of the lower portion of the prosthetic device when the spring just touches the lower portion and has not yet been compressed, or the point when the ankle is standing straight up.

Because the spring is compliant, as the prosthetic device moves past the neutral position, the load bearing face of the spring deflects in response to contact with the lower portion of the prosthetic device. At the same time, the angle of rotation of the ankle joint changes. The more force that is applied to change the angle of rotation of the ankle joint, the more the force measuring spring flexes. A magnetic angle sensor detects the change in the angle of rotation of the ankle joint and, based on the known compliance of the spring, the applied torque can be calculated, as described above.

In a previous version of the prosthetic device, the function of the force measuring spring was provided by a deflection of the structure under load. This design however, was not optimal. The structure of the device needs to be strong and stiff, for structural purposes, but springy and compliant for measurement purposes. Additionally, the spring constant was dependent on many factors, including, for example, tolerances on complex parts, details of bolted joints, etc. Creating the separate force measuring spring of the present invention allows the structure to be made as stiff as necessary while making the spring more compliant and the deflections of the spring more repeatable.

Various embodiments may be generally directed to prosthetic devices for lower leg amputees. The prosthetic device may comprise an upper member for attachment to the leg of the amputee, and a lower member for contact with the ground, wherein the upper member and lower member are movably attached to each other. In some embodiments, the upper member and lower member may be attached by a linkage allowing complex motion between the upper member and the lower member. It should be realized by one of skill in the invention that the terms "upper member" and "lower member" may be used interchangeably herein, and may also be referred to as "first member" and/or "second member".

In one embodiment, the upper member and lower member are rotatably attached at a pivot point. The pivot point of connection between the upper member and lower member simulates the ankle joint of a human foot. In some embodiments, the spring member is fixed to the upper member of the prosthetic device. In other embodiments, the spring member may be fixed to the lower member of the prosthetic device. In yet another embodiment multiple spring members could be affixed to both the upper member and the lower member of the device.

In certain embodiments, the lower member is provided with a contact area which will contact the spring member as the lower member of the prosthetic device is rotated with respect to the upper member of the prosthetic device to a toe-up configuration. In a complementary embodiment, the spring member is provided with a complementary area to receive the contact area of the lower member. It should be realized by one of skill in the art that, in an embodiment wherein the spring member is fixed to the lower member of the prosthetic device, the upper member will be provided with the contact area for contacting the spring member. In some embodiments, the contact areas of the upper member and lower member may be flat, while in other embodiments, the contact areas of the upper member and lower member may have complementary curved surfaces to reduce friction between the parts.

In various embodiments, the lower member will contact the spring member only after rotating through several degrees of rotation. In some embodiments, the range of rotation between the lower member and the upper member may be between 5° and 10° before the lower member contacts the spring member. Thus, in a neutral or toe-down configuration, the prosthetic device is provided with a gap between the contact area of the lower member and the contact area of the spring member.

In various embodiments, after the lower member has contacted the spring member, the spring member will deflect or flex with an approximately linear motion. In some embodiments, the upper portion of the prosthetic device may be configured with a hard stop member which limits the movement of the spring as it is compressed, and the spring member may be compressed until reaching the hard stop.

One of skill in the art will readily realize that, as the lower member is contacting the spring member via a rotating motion, the deflection of the spring member cannot be perfectly linear without relative motion between the contact faces. However, the range of deflection for the spring member is so small prior to contacting the hard stop fixed to the upper member, that its motion can be modeled as linear for purposes of calculating the torque applied to push the prosthetic device into a toe-up configuration. In some embodiments, the deflection of the spring member may be less than 1 mm prior to contacting the hard stop.

In various embodiments, the contact area of the spring member may be provided with a contact plate attached to the spring member. The contact plate may be disposed such that the contact face of the lower member contacts only the contact plate attached to the spring member. In some embodiments, the contact plate attached to the spring member is composed of a thermoplastic compound. In some embodiments, the thermoplastic compound is an acetal homopolymer. In other embodiments, the contact plate, as realized by one of skill in the art, may be made of any suitable material, and the invention is not meant to be limited to the exemplary materials mentioned.

In certain embodiments, the spring member may be equipped with a mounting plate for attachment to the prosthetic device. As previously discussed, in one embodiment, the spring member is fixed via the mounting plate to the upper member of the prosthetic device, but in other embodiments may be fixed to the lower member of the prosthetic device.

In some embodiments, the spring member may further comprise a distal end having a first arm, the first arm defining a contact portion, a second arm, connected to the first arm, a third arm, connected to the second arm at the opposite end of the connection of the second arm to the first arm, a fourth arm connected to the third arm at the opposite end of the connection of the third arm to the second arm, and a mounting plate connected to the fourth arm at the opposite end of the connection of the fourth arm to the third arm. In some embodiments, the angles of connection between the arms of the spring member are substantially 90°.

In some embodiments, the spring member may be in the general shape of a question mark character ("?"), wherein the fourth arm corresponds to the straight portion of the question mark character, and the third, second and first arms correspond to the curved portion of the question mark character. In certain embodiments, the first and third arms extend along parallel axes, the axes, being substantially orthogonal to a force exerted on the contact portion of the first arm of the spring member when the contact face makes contact with the corresponding contact face of the lower member.

In some embodiments, the spring member may be composed of titanium, although one of skill in the art should realize that the invention is not meant to be limited to that composition, but that any suitable material could be used to form the spring member.

In certain embodiments, the spring member is attached in a fixed manner to the upper member of the prosthetic device. Although any known method of attachment may be utilized, the exemplary embodiment disclosed herein consists of a plurality of posts which engage holes in a portion of the upper member and a plurality of bolts which fixedly attach the spring member to the upper member. In certain embodiments of the invention, the spring member is attached to a structural member which forms a portion of the outer skin of the upper portion of the prosthetic device.

In certain embodiments of the invention, a pair of spring members is used, one disposed in the central portion of the prosthetic device and one disposed in the peripheral portion of the prosthetic device, corresponding to the inside of the calf of the amputee and the outside of the calf of the amputee respectively. In such cases, it would be realized by one of skill in the art that the lower member will have a pair of contact faces to contact the corresponding pair of spring members. In some embodiments, the upper member will be configured with a pair of hard stops, each corresponding to one of the pair of spring members.

In certain embodiments of the invention, the pivot point between the upper member and lower member of the prosthetic device may be configured with an angle sensor for measuring the angle between the upper member and lower member. In some embodiments, the output from the angle sensor will be utilized as an input to a model controlling an actuator control circuit, which may in turn control and actuator to apply torque to the pivot point. In some embodiments, the angle sensor will be a commercially available magnetic type sensor, but one of skill in the art would realize that any sensor capable of measuring the rotation may be used. In some embodiments, the actuator may be a motor.

In certain embodiments of the invention, the prosthetic device further comprises a processor running software implementing a model to control an actuator control circuit. The model may take as input the angle of the lower member with respect to the upper member as measured by the angle sensor. Additionally, the model is aware of the spring constant of the spring member and the amount of force required to deflect the spring member from its neutral position until it contacts the hard stop, and thus can calculate the torque required based on the amount that the spring deforms, as measured by the rotation of the lower structure relative to the upper structure.

The actuator control circuit, in some embodiments, is configured to control an actuator applying torque to the pivot point. In some embodiments, the actuator may apply torque to the pivot point via a linkage, for example, a motor may apply torque to a belt drive which drives a ball screw attached to the lower member. The actuator control circuit, in some embodiments, causes the actuator to apply torque to the pivot point in accordance with the model. In some embodiments, the model approximates the torque applied to a human ankle by the Achilles tendon and calf muscle, wherein the angle sensor is as an input in the calculation of the torque, which is used as an input to the model to determine the amount of counter-torque needs to be applied by the actuator.

In some embodiments, the processor may execute software for performing the steps of a method, the method including taking as input the calculated torque generated by the relative movement of the upper and lower members as measured by the angle sensor. The calculation of the torque is based on the rate of rotation and the known compliance of the spring member, and controlling an actuator via the actuator control circuit to apply a counter-torque to the pivot point based on a model approximating the torque applied to a human ankle by the Achilles tendon and the calf muscle.

FIG. 1(a) shows a side view of certain portions of the prosthetic device 100 of the present invention and represents an exemplary embodiment that may be representative of various embodiments. The prosthetic device may consist of upper member 102 rotatably connected to lower member 104 at pivot point 105. Spring member 106 is fixed to upper member 102. Upper member 102 may be configured with hard stop 108, to limit the deflection of spring member 102. In certain embodiments, the limit of the range of deflection of spring member 102 may be less than 1 mm. Spring member 102 may be configured with contact plate 109 composed of a thermoplastic compound and utilized to reduce wear on spring member 102 and to reduce noise. Lower member 104 may be configured with contact face 117, which contacts contact plate 109 as lower member 104 rotates in a clockwise direction (in this view) with respect to upper member 102.

FIG. 1(a) shows the prosthetic device in a toe-up configuration where in the contact face 117 of lower member 104 is in contact with spring member 106. As can be seen, there is no gap between the contact face 117 of lower member 104 and the contact plate 109 of spring member 106. As can also be seen, a gap 107 still remains between spring member 106 and hard stop 108, indicating that spring member 106, as shown in the figure, has not deflected through its full range of motion. A person of skill in the art would realize that the configuration of prosthetic device 100 shown in FIG. 1(a) represents the phase of the walking cycle wherein the foot is in contact with the ground and wherein the center of mass of the walker is generally in front of pivot point 105.

Angle sensor 122, located at pivot 105 is configured to measure the angle of rotation between lower member 104 and upper member 102. As previously discussed, in certain embodiments, the output from angle sensor 122 is utilized to calculate the torque generated by the rotation, which is used as input to the model controlling the actuator control circuit. It should be realized by a person of skill in the art that many other parts comprising prosthetic device 100 have been removed from the figure to show the relationship between upper portion 102, lower portion 104 and spring member 106.

Figure 1B:
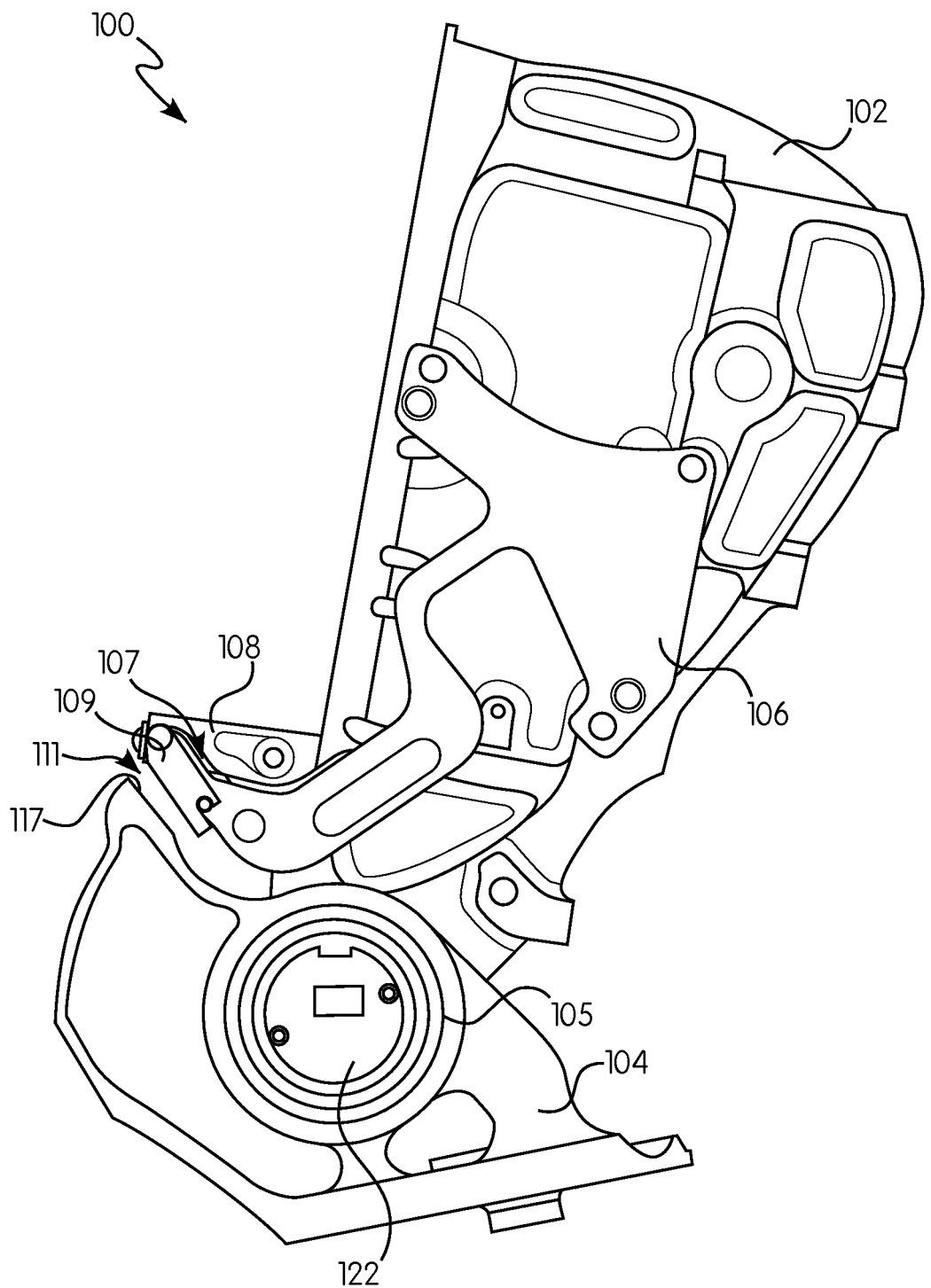
FIG. 1(b) is a side view of a prosthetic device having an embodiment of the force measuring spring of the present invention installed thereon, in a second position.

FIG. 1(b) shows prosthetic device 100 wherein the lower member 104 has rotated counterclockwise (in this view) to a neutral or toe-down position with respect to the upper member 102. In such a configuration, the gap 111 between the lower member 104 and the spring member 106 can clearly be seen, as can the gap 107 between the spring member 106 and hard stop 108. In this configuration, spring member 106 is experiencing no deflection. As a person of skill in the art would realize, this configuration of prosthetic device 100 represents the phase of the walking cycle wherein the foot is off the ground, or wherein the foot is on the ground and the center of mass of the walker is generally in back of pivot point 105.

Figure 2A:
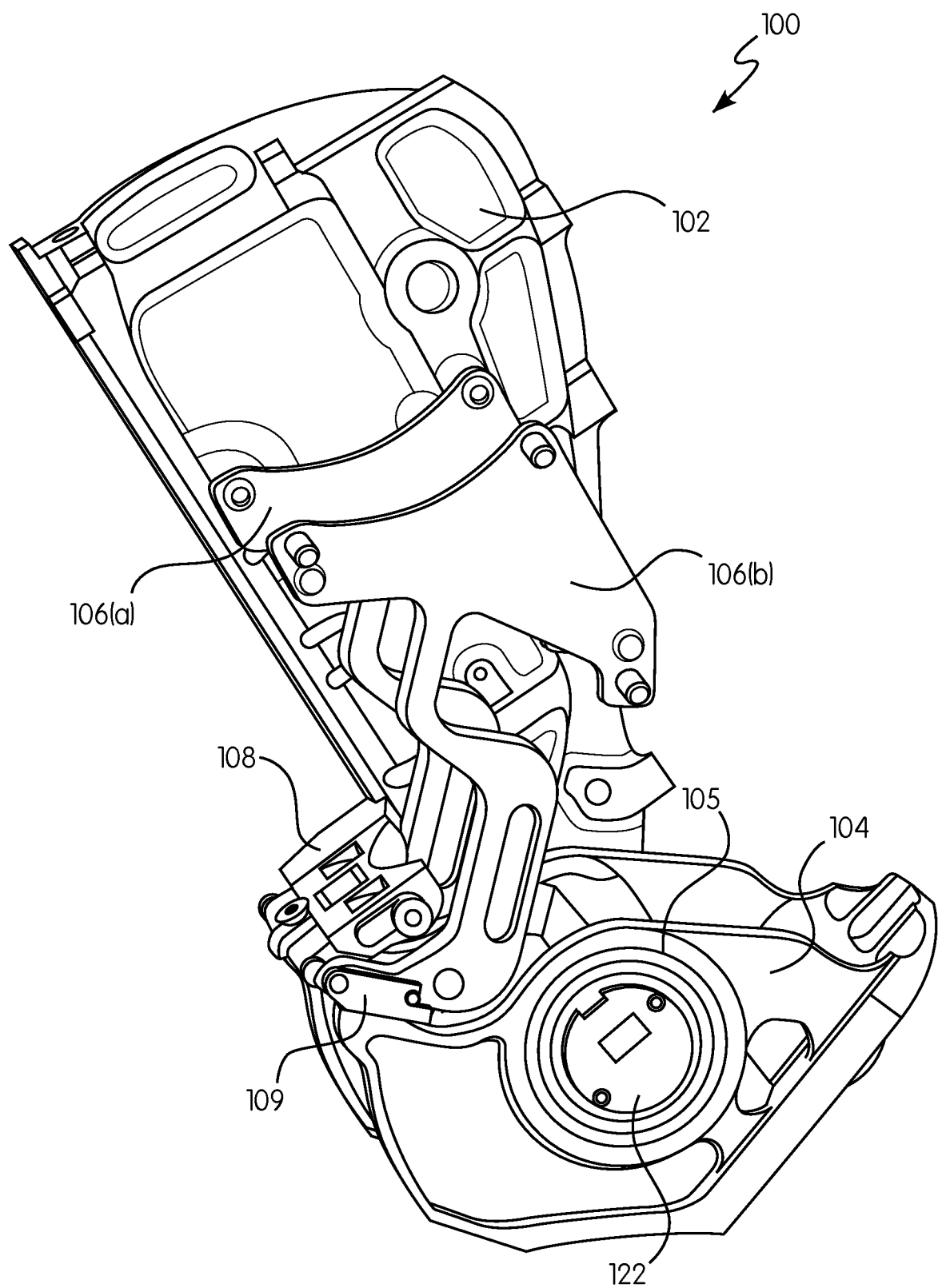
FIG. 2(a) is an upper perspective view of a prosthetic device showing use of a pair of force measuring springs of the present invention, in a first position.

FIG. 2(a) shows an upper perspective view of prosthetic device 100. In this view, the embodiment wherein a pair of spring members 106 is utilized can clearly be seen. In the embodiment shown, spring member 106(a) represents the peripheral positioning and spring member 106(b) a represents central the positioning of the spring members. It should be realized by one of skill in the art that spring member 106(a) would be connected to a peripheral structural member of upper member 102 and that spring member 106(b) would be connected to a central structural member of upper member 102. In FIG. 2(a), prosthetic device 100 is shown in the toe-up configuration, identical to the configuration shown in FIG. 1(a).

Figure 2B:
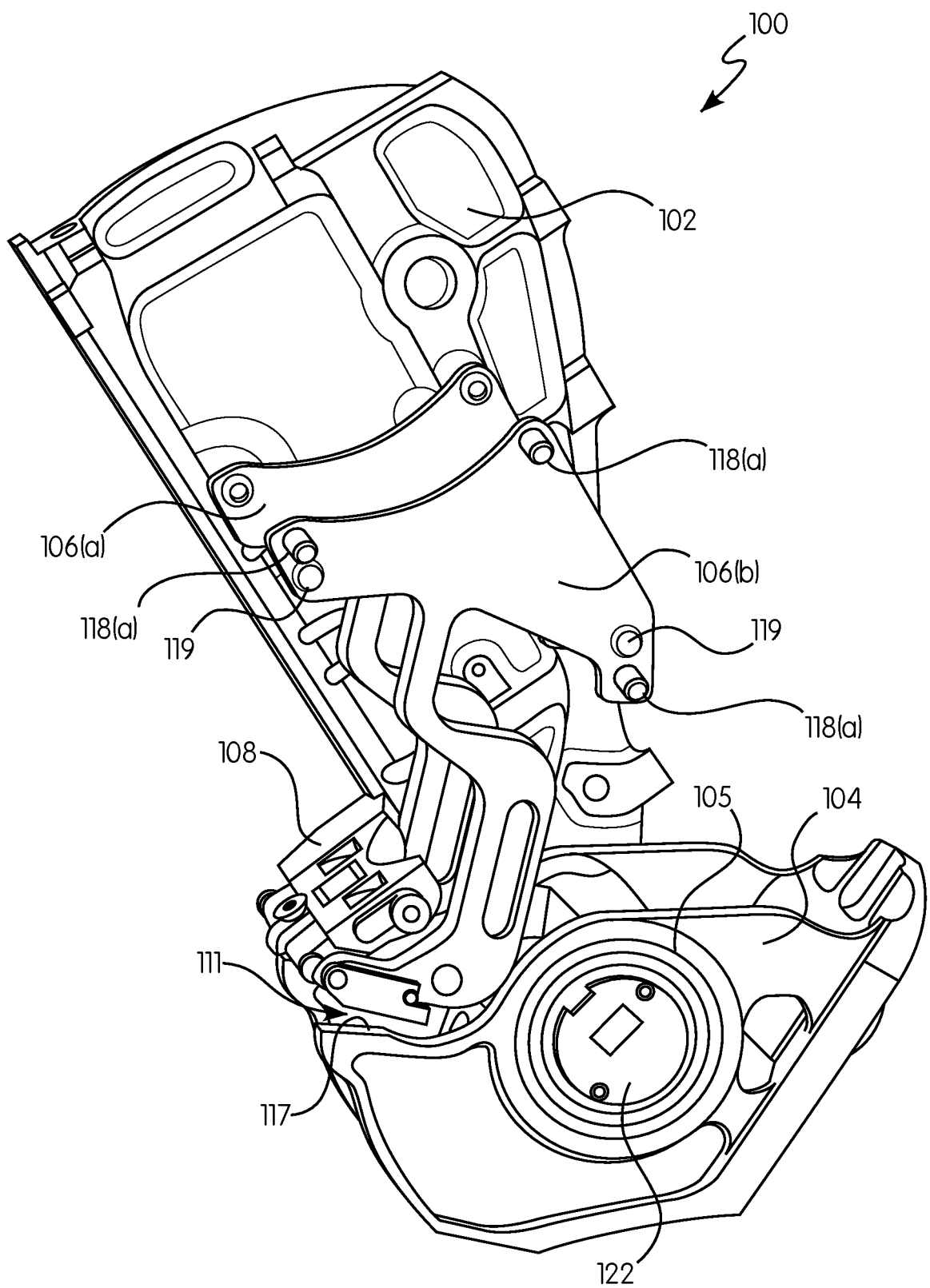
FIG. 2(b) is an upper perspective view of a prosthetic device showing use of a pair of force measuring springs of the present invention, in a second position.

FIG. 2(b) shows an upper perspective view of the prosthetic device 100 in the toe-down position, identical to the configuration shown in FIG. 1(b). In this view, contact face 117 of lower member 104 is clearly shown as not being in contact with contact plate 109 of spring member 106(b), as gap 111 between contact face 117 and contact plate 109 attached to spring member 106(b) can clearly be seen. In addition, gap 107 between spring member 106 and hard stop 108 can also clearly be seen. FIG. 2(b) shows a configuration of prosthetic device 100 wherein a pair of spring members 106(a) and 106(b) are utilized. As in previous views, it would be realized one by one of skill in the art, that prosthetic device 100 shown in the figure has been stripped of many parts to show only the parts pertinent to the present invention.

Figure 3:
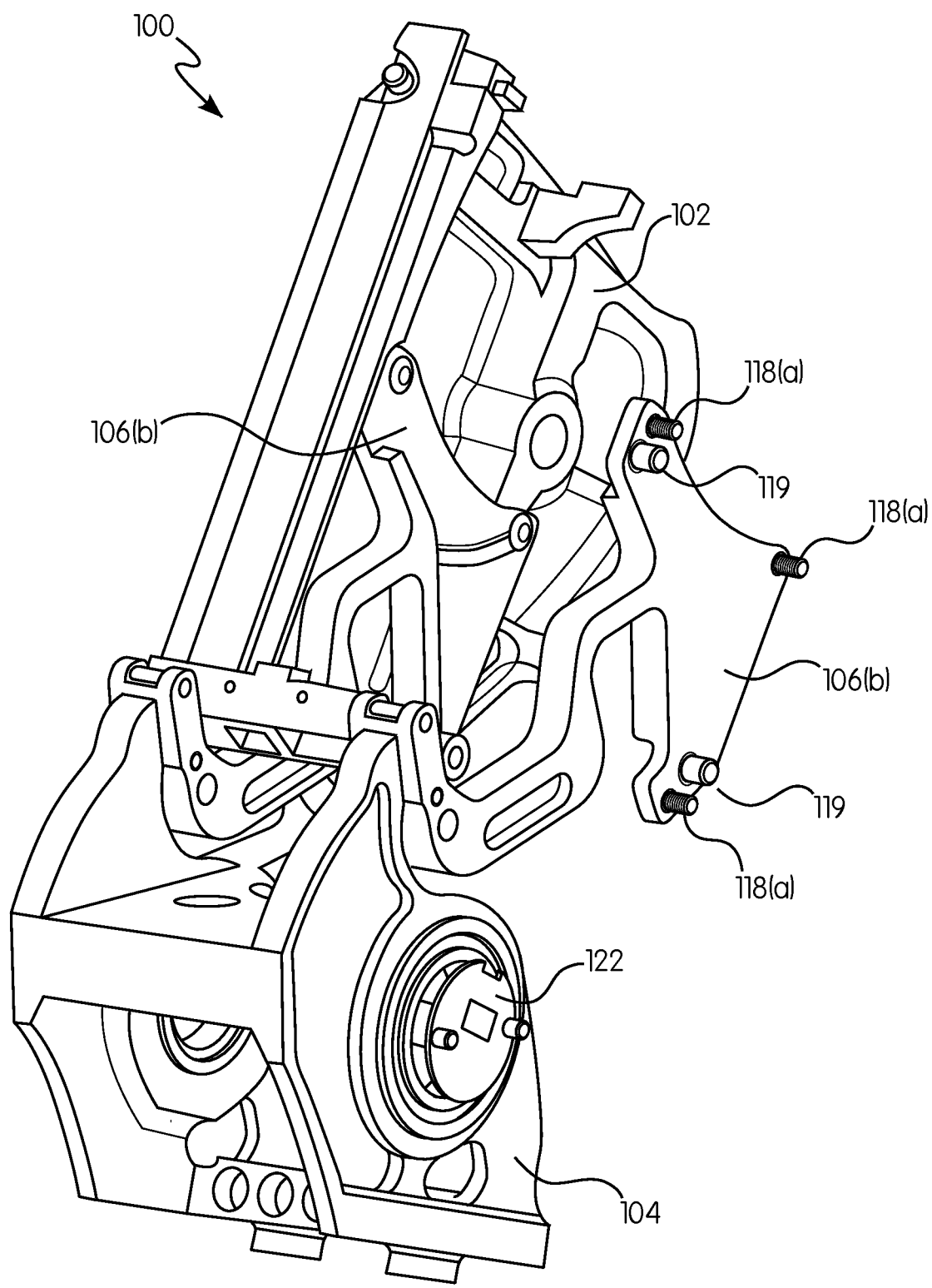
FIG. 3 is a lower perspective view of a prosthetic device showing use of a pair of force measuring springs of the present invention.

FIG. 3 shows prosthetic device 100 in a lower perspective view showing the configuration of lower member 104 in more detail. FIG. 3 also shows an embodiment wherein a pair of springs 106(a,b) have been utilized. In addition, shown in FIG. 3 are posts 119 and bolts 118(a) which are used to secure spring members 106(a,b) to peripheral and central structural members of upper member 102 respectively. In certain embodiments of the invention, posts 119 will fit into recesses (not shown) configured in the structural members of upper member 102, while bolts 118(a) will screw into threaded recesses (not shown) also located in structural members of upper member 102.

Figure 4:
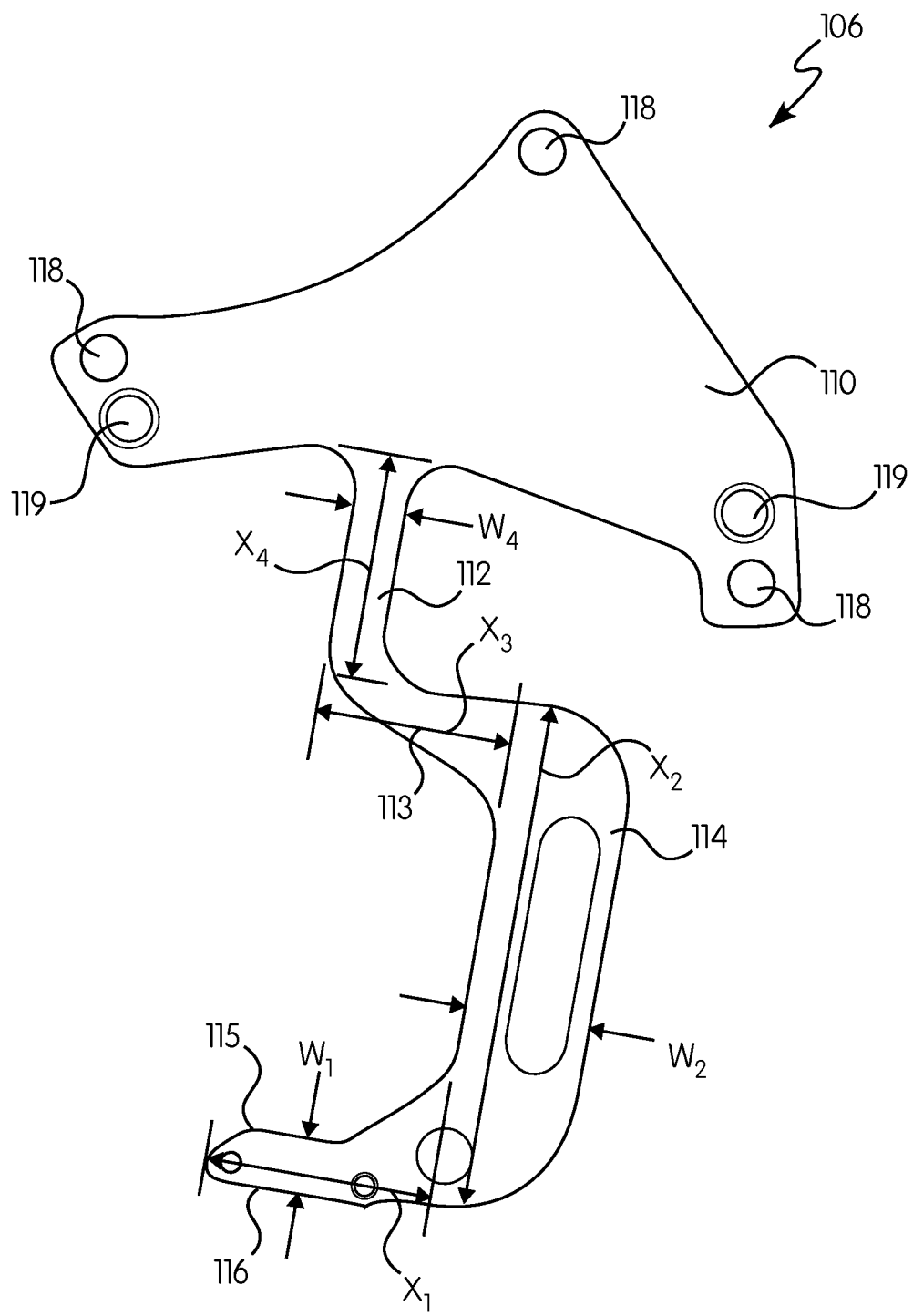
FIG. 4 is a side view of the force measuring spring of the present invention.

FIG. 4 shows a side view of spring member 106. Spring member 106 may be in the general shape of a question mark character ("?"). As can be seen, the distal end of spring member 106 includes a first arm 115 having width W1 and extending in a first linear direction of length X1. Spring member 106 then bends at a substantially 90° angle to a second arm 114, that has length W2 and extends in a second linear direction of length X2. The bend between the first arm 115 and the second arm 114 includes an outer face substantially in the shape of a curve and an inner face extending at a substantially 45° angle from the first arm 115 to the second arm 114.

Second arm 114 bends to connect at a substantially 90° angle to a third arm 113 extending in a third linear direction of length X3. The outer face and the inner face of the bend between second arm 114 and third arm 113 are substantially in the shape of non-concentric curves. The width of third arm 113 varies along length X3. The end of third arm 113 opposite the end of connection to the second arm 114 bends at a substantially 90° angle to connect to a fourth arm 114 which extends in a fourth linear direction of length X4. The outer face and inner face of the bend between third arm 113 and fourth arm 112 are substantially in the shape of curves.

First arm 115 and third arm 113 extended along axes which are substantially parallel to each other and which may be generally orthogonal to a force exerted on contact portion 116 of first arm 115. Second arm 114 and fourth arm 112 extend in linear directions which are substantially parallel to each other. Generally, the length of the second arm 114, X2, is greater than X1, X3 and X4. Additionally, the width of the second arm 114, W2, is greater than W1 and W4. Fourth arm 112 is connected to mounting plate 110, which may be of any general shape.

Mounting plate 110 is connected to fourth arm 112 and contains posts 119, which would be received in corresponding recesses in a structural member of upper member 102 and holes 118 through which bolts 118(a) (shown in FIG. 3) may be disposed to be received in threaded recesses in a structural member of upper member 102. In certain embodiments of the invention, all portions of spring member 106 may be composed of titanium, however as realized by one of skill in the art, any other material having similar properties may be utilized.

Spring member 106 in FIG. 4 is shown without contact plate 109, which would normally be disposed on first arm 115 at contact portion 116. In certain embodiments, the movement of contact portion 116 is generally linear and can be considered linear for purposes of input to the model controlling the motor control circuit.

Figure 5:
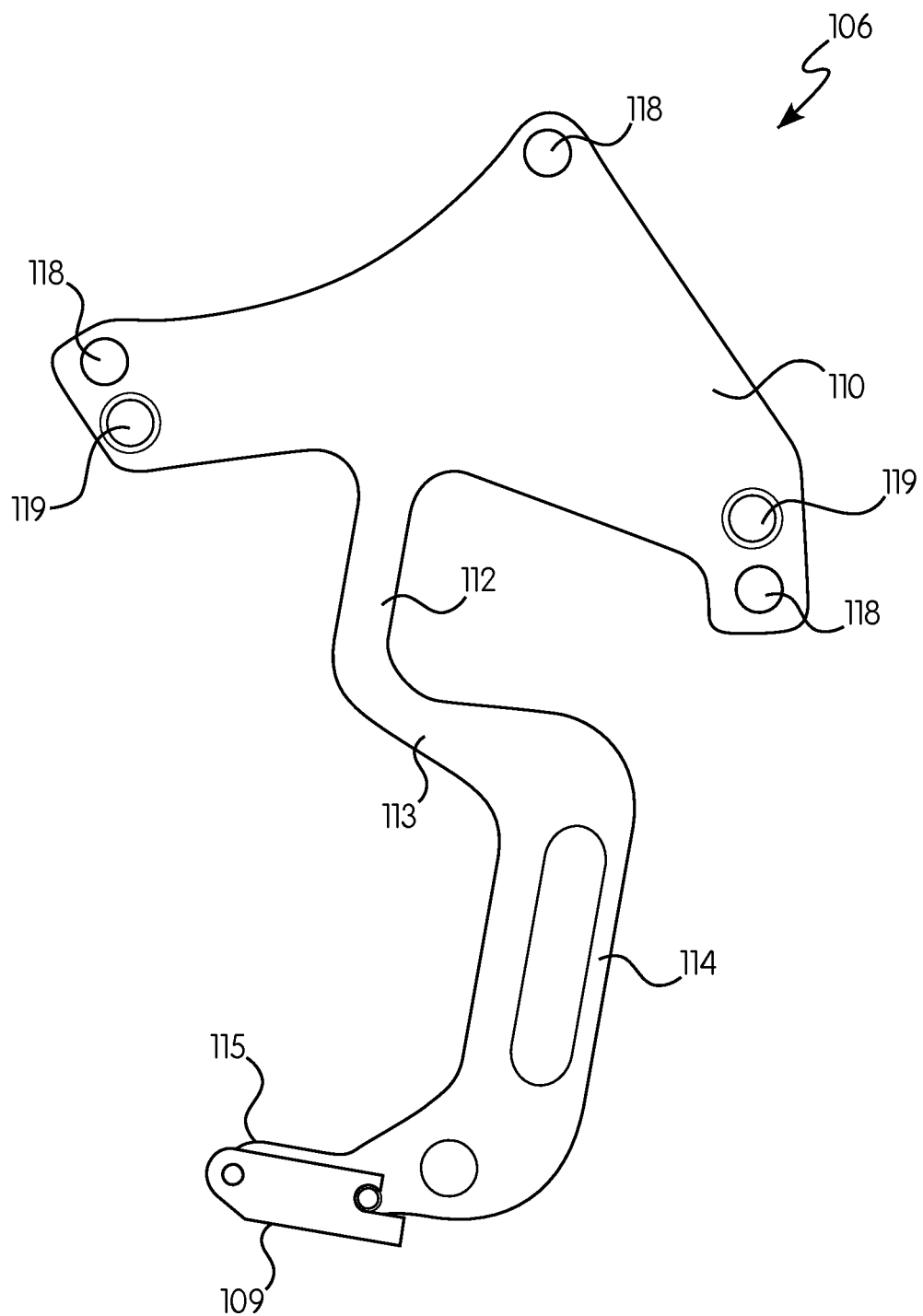
FIG. 5 is a side view of the force measuring spring of the present invention having additional hardware attached thereto.

FIG. 5 is a side view of spring member 106 showing contact plate 109 attached at contact portion 116 of first arm 115 of spring member 106. Contact plate 109, as previously discussed, is, in certain embodiments, composed of a thermoplastic compound, and in some embodiments the thermoplastic compound is an acetal homopolymer. In certain embodiments, contact plate 109 is disposed on the contact portion 116 of spring member 106 to reduce wear and tear on contact portion 116 and any noise generated as contact portion 116 is contacted by contact face 117 of lower member 104, which moves with a generally rotational motion.

Figure 6:
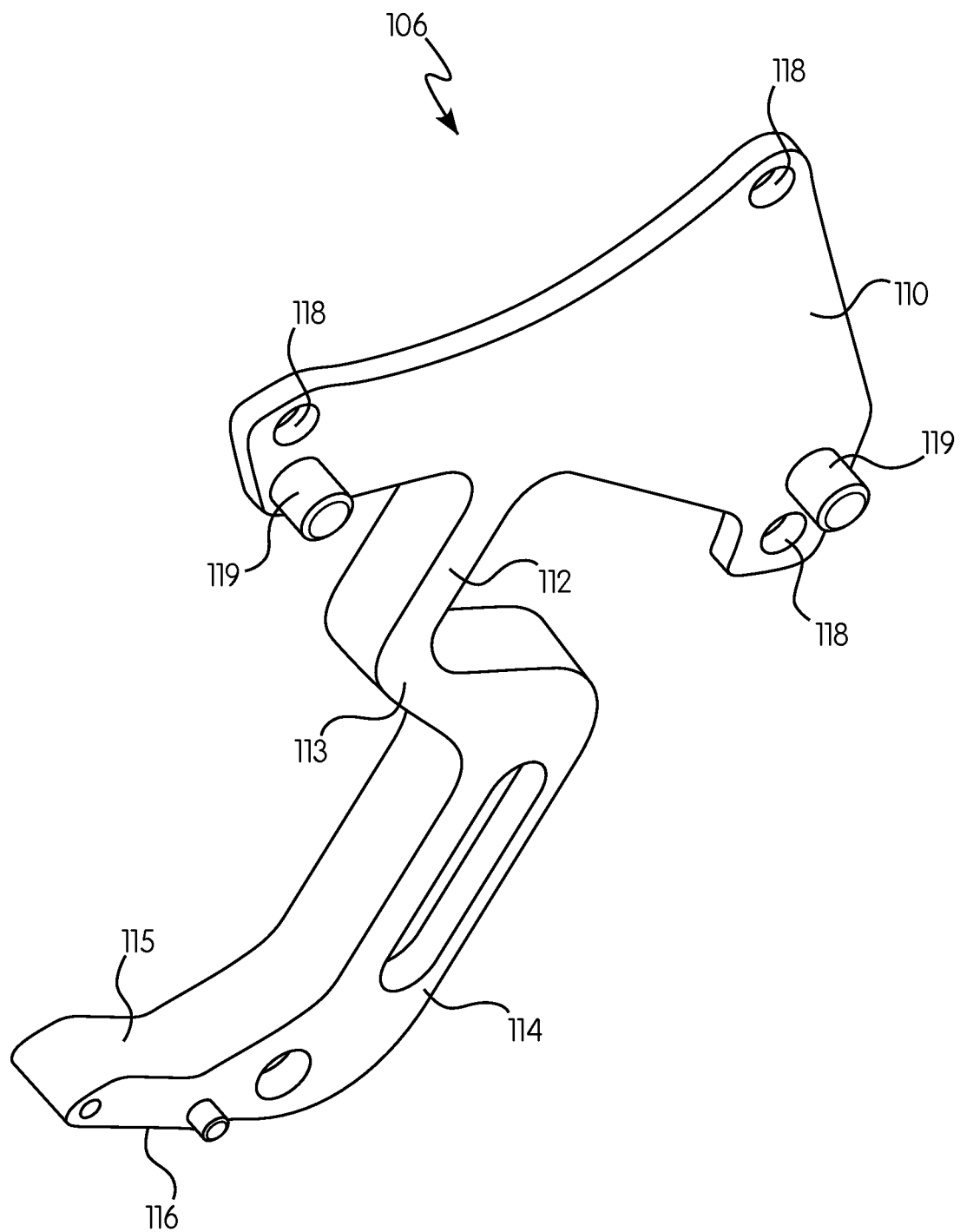
FIG. 6 is an upper perspective view of the force measuring spring of the present invention

FIG. 6 shows a perspective view of spring member 106 and is provided to show, in certain embodiments, the aspect ratio between the height and width of various portions of spring member 106.

Figure 7:
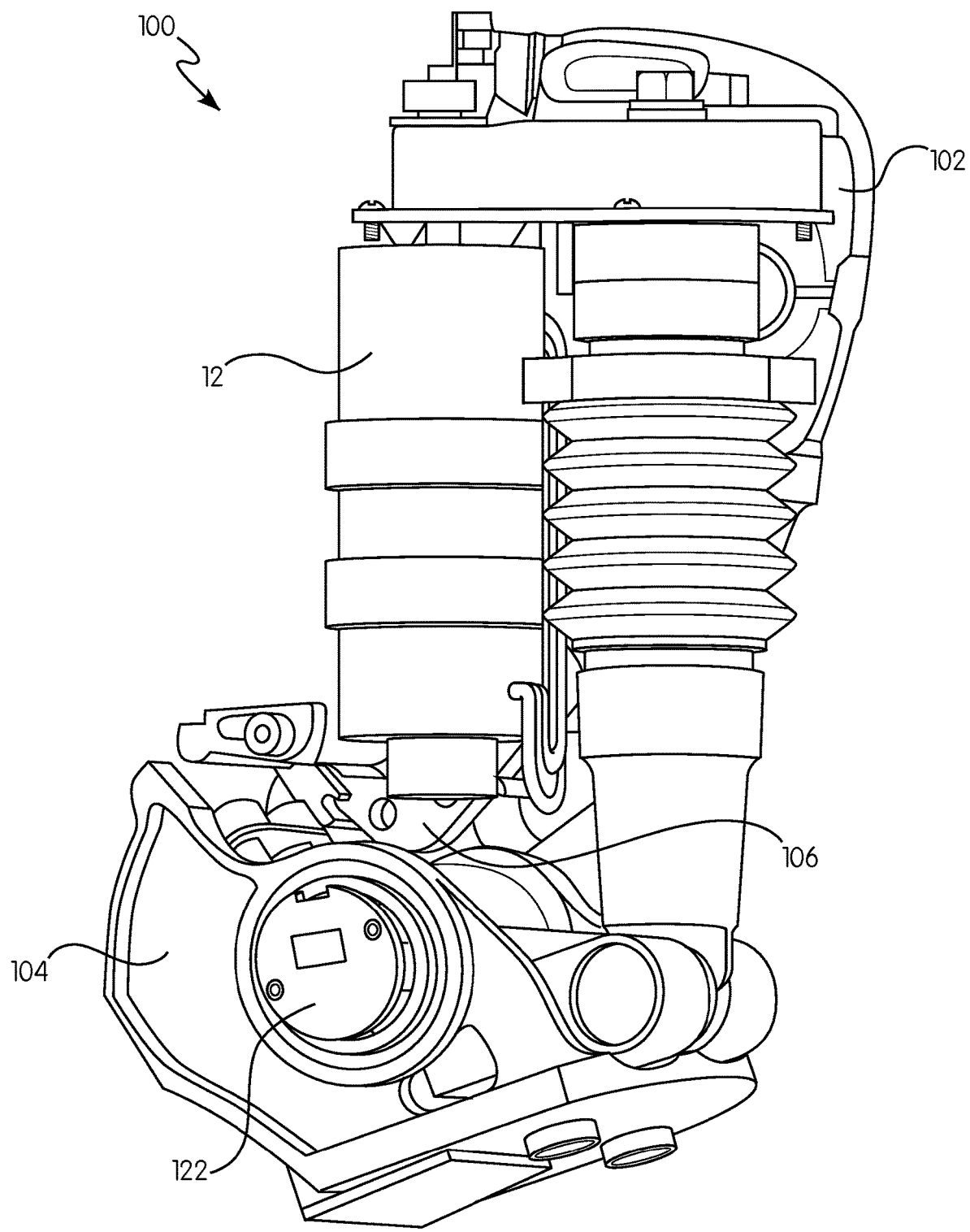
FIG. 7 is a rear perspective view of a prosthetic device showing the positioning of the motor elements.
Figure 8A:
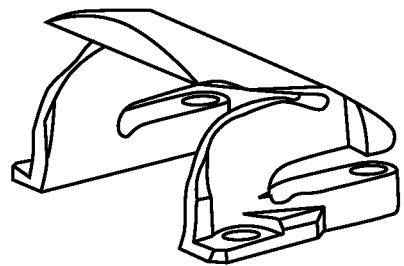
FIGS. 8(a-k) show alternate embodiments of the force measuring spring of the present invention.
Figure 8B:
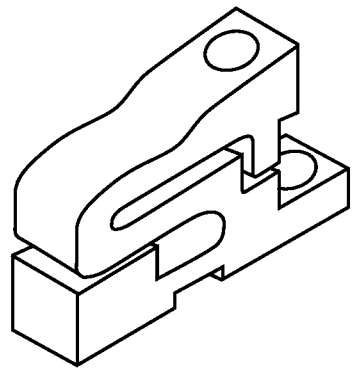
Figure 8C:
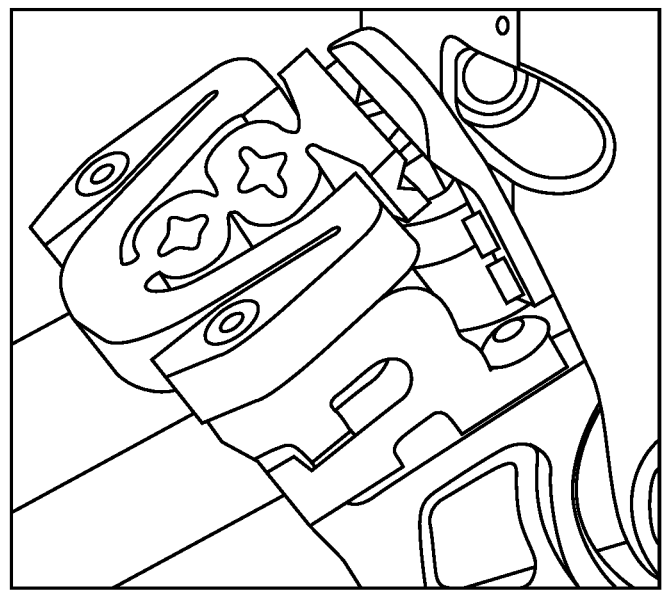
Figure 8D:
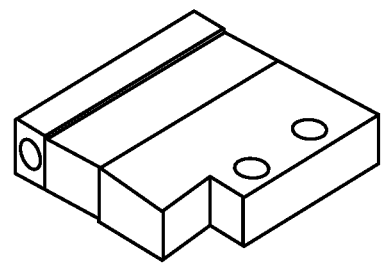
Figure 8E:
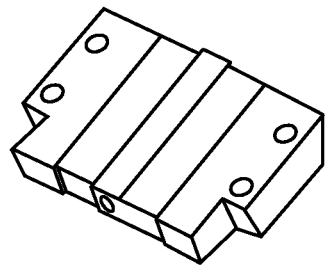
Figure 8F:
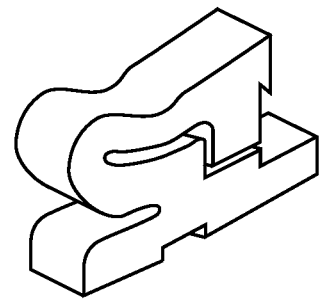
Figure 8G:
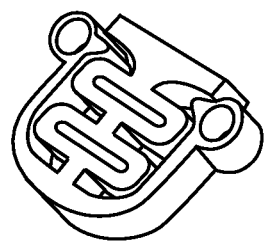
Figure 8H:
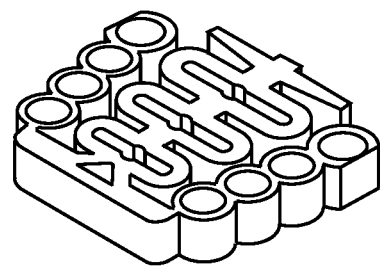
Figure 8I:
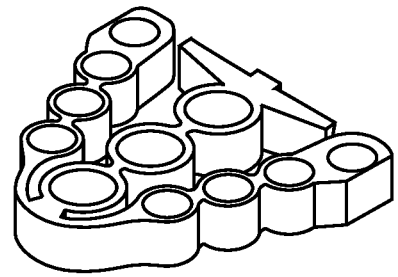
Figure 8J:
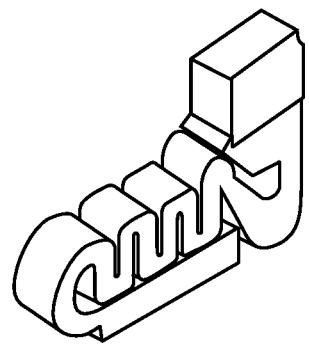
Figure 8K:
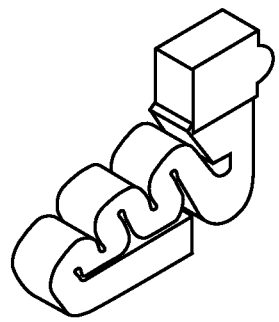

FIG. 7 shows prosthetic device 100 having motor 120 and connection hardware for the actuator 120 shown in situ. As would be realized one of skill in the art, this configuration of actuator 120 and connection hardware is only exemplary in nature and that any configuration may be utilized for purposes of this disclosure. It would also be realized by one of skill in the art that many additional parts may be provided in prosthetic device 100, but have been removed to show the relationship between parts of prosthetic device 100 pertinent to this disclosure.

FIGS. 8(a-k) show other embodiments of spring member 106. In some embodiments, a single spring member may be connected to the dorsal portion of prosthetic device 100 instead of having a pair of spring members connected to the central and peripheral sides of prosthetic device 100.

Figure 9:
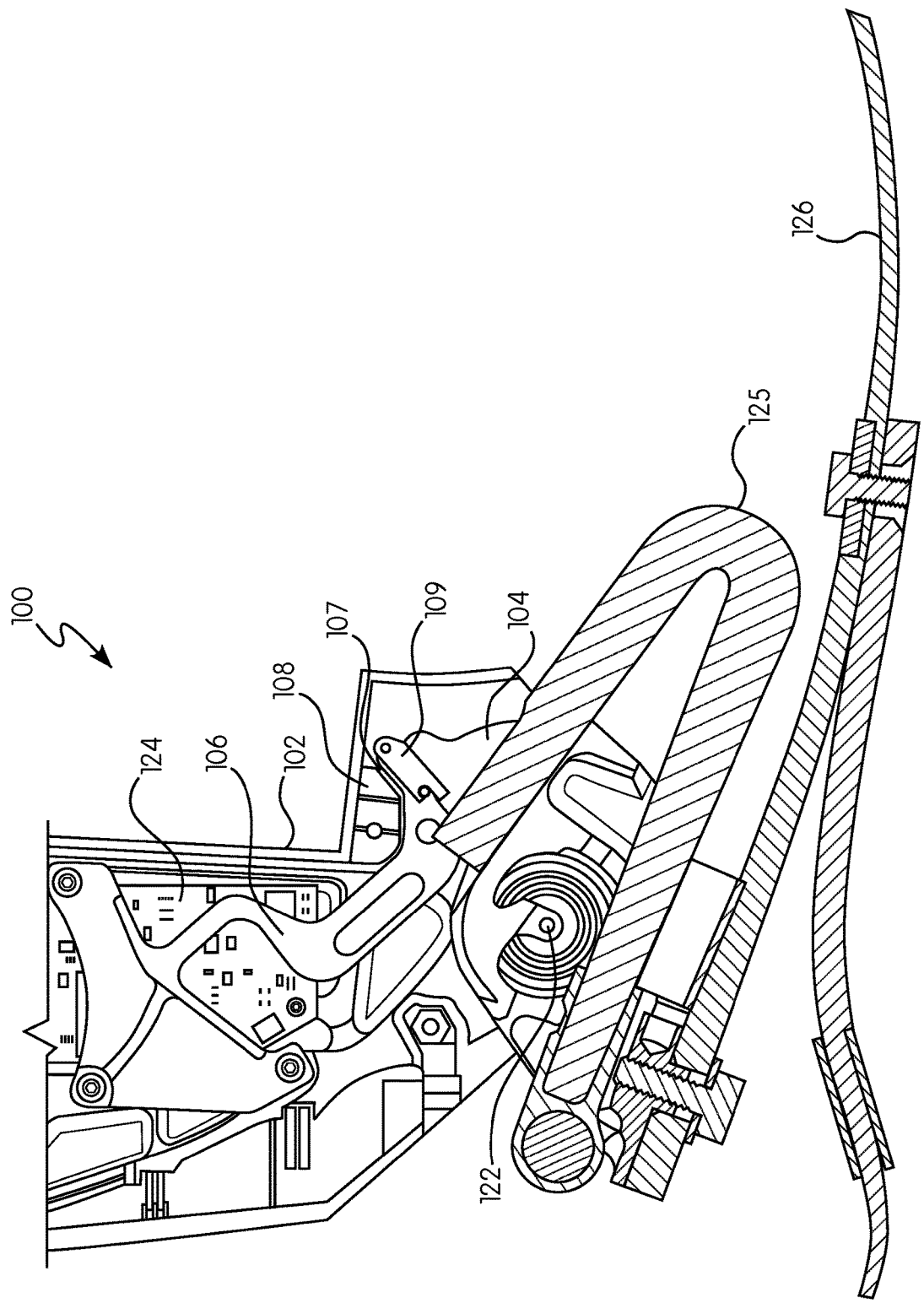
FIG. 9 shows a side view of the prosthetic device showing multiple parts which were removed in previous figures for clarity.

FIG. 9 shows a side section view of the prosthetic device showing multiple parts which were removed in previous figures for clarity. Prosthetic device 100 is shown, in this embodiment, in a toe-up configuration during the portion of the walking phase wherein the walker is pushing forward with the leg to which the prosthetic device 100 is connected. As such, lower portion 104 is contacting spring member 106. As shown in this figure, the gap 107 between spring member 106 and hard stop 108 is still open, indicating that prosthetic device 100 is shown in a configuration wherein spring member 106 has not been deflected through its full range of motion. Also shown in this figure, and not shown in previous figures, are actuator control circuitry 124, spring 125 and ground contact member 126. In this figure, these parts are shown merely to illustrate their placement with respect to parts which are pertinent to the present invention. It should be realized by one of skill in the art said no limitations are meant to be imposed on the invention as a result of any placement of parts shown in any figures of the application.

Although the subject matter has been described in language specific to various structural features and configurations, it is to be understood that the subject matter defined in the appended claims is not necessarily limited to the specific features or configurations described above. Rather, the specific features and configurations described above are disclosed as example forms of implementing the claims.

We claim:

1. A prosthetic, orthotic, or exoskeletal (POE) device comprising:
   a first member;
   a second member moveably connected to the first member through a rotatable joint configured to augment or replace a human joint, the joint applying a torque to the POE device during at least a part of its rotation; and
   a spring member fixed to the first member, the second member directly contacting the spring member during at least a portion of the movement of the second member with respect to the first member, the spring member configured to deflect from a neutral position when contacted by the second member and providing resistance to the rotation of the second member in relation to an amount of the torque.

2. The POE device of claim 1, wherein at least one of the second member or the spring member comprises a contact plate located between the spring member and the second member.

3. The POE device of claim 2, wherein the spring member comprises the contact plate, and the contact plate is attached to the spring member at a point of contact between the spring member and the second member.

4. The POE device of claim 2, wherein the second member comprises the contact plate, and the contact plate is attached to the second member at a point of contact between the spring member and the second member.

5. The POE device of claim 4 wherein a contact face of the contact plate is composed of a thermoplastic compound.

6. The POE device of claim 5 wherein the thermoplastic compound is acetal homopolymer.

7. The POE device of claim 1 further comprising a hard stop, fixed to the first member, the hard stop limiting the deflection of the spring member and the rotation of the second member.

8. The POE device of claim 7, wherein deformation of the spring member between the neutral position and the hard stop is approximately linear.

9. The POE device of claim 7, wherein the spring member deflects less than 1 mm before contacting the hard stop.

10. The POE device of claim 1 wherein the second member and first member have a rotational motion between 5 and 10 degrees with respect to each other before the second member contacts the spring member.

11. The POE device of claim 1, wherein the spring member is attached on one side of the first member, the apparatus further comprising a second spring member attached to the opposite side of the first member.

12. The POE device of claim 1 wherein the spring member comprises:
a first arm;
a second arm connected to the first arm;
a third arm connected to the second arm;
a fourth arm connected to the third arm; and
a mounting plate, connected to the fourth arm;
wherein the first arm and third arm extend along axes which are substantially parallel to each other, and wherein the second arm in the fourth arm extend along axes which are substantially parallel to each other.

13. The POE device of claim 12 wherein:
the second arm connects to the first arm at a substantially 90° angle;
the third arm connects to the second arm at a substantially 90° angle; and the
fourth arm connects to the third arm at a substantially 90° angle.

14. The POE device of claim 12, wherein the spring member is connected to the first member via the mounting plate.

15. The POE device of claim 1, wherein the spring member is composed of titanium.

16. A method comprising:
providing a POE device according to claim 1; and
causing the second member to move with respect to the first member and directly contact the spring member, the movement deflecting the spring member from the neutral position.

17. The method of claim 16, further comprising:
measuring an angle between the first member and the second member;
providing the measured angle to a model for controlling an actuator control circuit; and
controlling the actuator based on an output of the model to apply torque to a pivot point between the first member and the second member.

18. The method of claim 16, wherein the deflection of the spring member from the neutral position is approximately linear between the neutral position and a hard stop.

19. The method of claim 16, further comprising attaching the first member to a leg of an amputee.

20. The POE device of claim 1, further comprising an actuator configured to apply a counter-torque to the rotatable joint.

21. The POE device of claim 20, further comprising a controller programmed with instructions configured to cause the POE device to:
determine the amount of the torque based at least in part on the deflection of the spring member;
calculate the counter-torque based on the determined amount of torque; and
cause the actuator to provide the calculated counter-torque.

22. The POE device of claim 21, wherein determining the amount of torque comprises measuring an angular rotation of the actuator.

* * * * *